United States Patent
Facchetti et al.

(10) Patent No.: US 11,813,349 B2
(45) Date of Patent: Nov. 14, 2023

(54) HAIR COLOURING COMPOSITIONS IN GEL OR EMULSION-GEL FORM

(71) Applicant: BEAUTY & BUSINESS S.p.A., Milan (IT)

(72) Inventors: Emanuela Facchetti, Romano di Lombardia (IT); Antonio Consoli, Urgnano (IT); Katiuscia Grevalcuore, Bergamo (IT); Monica Besozzi, Pontirolo Nuovo (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 0 days.

(21) Appl. No.: 18/062,621

(22) Filed: Dec. 7, 2022

(65) Prior Publication Data

US 2023/0190624 A1    Jun. 22, 2023

(30) Foreign Application Priority Data

Dec. 21, 2021  (IT) ................. 102021000031967

(51) Int. Cl.
| | | |
|---|---|---|
| A61Q 5/10 | (2006.01) | |
| A61K 8/73 | (2006.01) | |
| A61K 8/81 | (2006.01) | |
| A61Q 5/06 | (2006.01) | |

(52) U.S. Cl.
CPC .............. *A61K 8/73* (2013.01); *A61K 8/8135* (2013.01); *A61Q 5/065* (2013.01); *A61Q 5/10* (2013.01); *A61K 2800/4322* (2013.01)

(58) Field of Classification Search
CPC .................... A61K 8/73; A61K 8/8135; A61K 2800/4322; A61Q 5/065; A61Q 5/10
USPC ............................................................ 8/405
See application file for complete search history.

(56) References Cited

U.S. PATENT DOCUMENTS

| | | |
|---|---|---|
| 2016/0279036 A1 | 9/2016 | Schoepgens et al. |
| 2017/0105921 A1 | 4/2017 | Fabbi et al. |
| 2018/0140531 A1 | 5/2018 | Singer et al. |

FOREIGN PATENT DOCUMENTS

| | | | | |
|---|---|---|---|---|
| CN | 110638667 A | 1/2020 | | |
| WO | WO 2012084410 A2 * | 6/2012 | ............... | A61Q 5/12 |

OTHER PUBLICATIONS

Search Report and Written Opinion of IT 202100031967 dated Jul. 13, 2022.

\* cited by examiner

*Primary Examiner* — Eisa B Elhilo
(74) *Attorney, Agent, or Firm* — SILVIA SALVADORI, P.C.; Silvia Salvadori

(57) ABSTRACT

The invention relates to hair colouring compositions in gel or emulsion-gel form containing no ethoxylated additives, ethanolamine or polyethylene glycols.

7 Claims, 1 Drawing Sheet

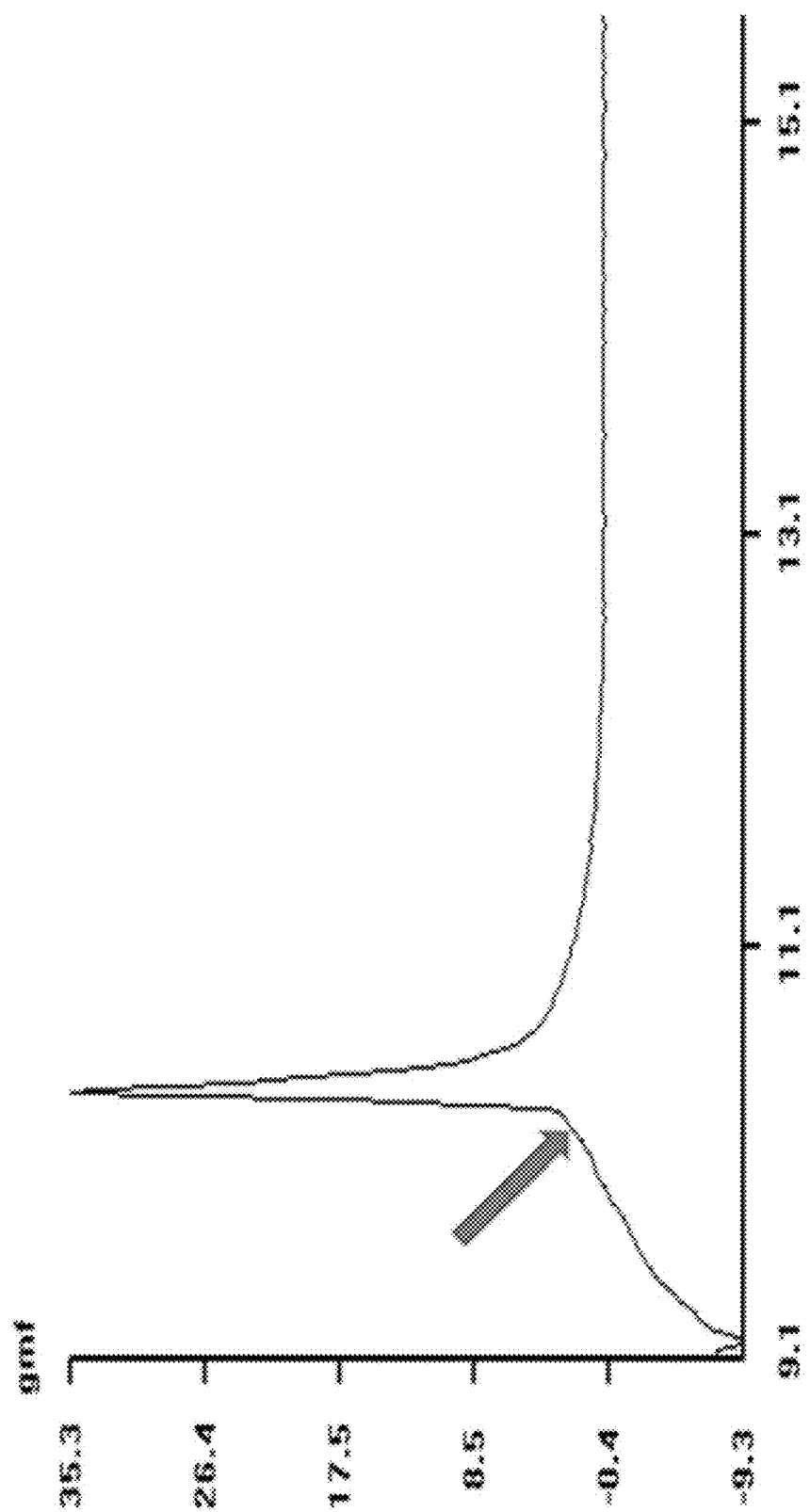

HAIR COLOURING COMPOSITIONS IN GEL OR EMULSION-GEL FORM

This application claims priority to and the benefit of Italian Patent Application no. 102021000031967, filed Dec. 21, 2021, the content of which is incorporated herein by reference in its entirety.

The invention relates to hair colouring compositions in gel or emulsion-gel form containing no ethoxylated additives, ethanolamine or polyethylene glycols.

Prior Art

Ethoxylation, a reaction between ethylene oxide and organic substrates with hydroxyl or carboxyl functions, is used for the manufacture of compounds widely used in the cosmetic industry, such as surfactants, viscosity-controlling agents and emulsifiers. For example, the most common non-ionic surfactants, which are advantageous in many applications due to their compatibility in various systems and better resistance to metal cations and electrolytes, are obtained by ethoxylation of fatty alcohols, fatty acids and ethoxylated triglycerides: examples of ethoxylated non-ionic surfactants include ceteareth-16, ceteareth-18, ceteareth-20 and ceteareth-50, PEG-20 stearate, PEG-40-hydrogenated castor oil, laureth-3 and laureth-2.

Ethylene oxide is also used for the manufacture of other additives widely used in the cosmetic and pharmaceutical industries, such as polyethylene glycols and ethanolamine, the latter being a common alkalising agent used in hair colouring preparations.

Worldwide production of ethoxylates amounts to several million tonnes per annum, with a significant impact on the carbon footprint, as ethylene oxide is produced from ethylene derived from fossil hydrocarbons. The alternative production from ethanol obtained from plant biomasses, developed by Croda Inc. from 2018, is insufficient to meet the huge market demand for ethoxylates.

Another environmental problem associated with the use of ethylene oxide of any origin is the presence of 1,4-dioxane as a reaction by-product.

1,4-Dioxane, classified as toxic according to the criteria specified in REACH Annex XIII and as a category 2 carcinogen pursuant to CLP (Regulation (EC) No 1272/2008), is highly diffusible in water environment and difficult to remove in water purification processes.

For that reason, many regulatory agencies have set very strict limits on the presence of 1,4-dioxane in cosmetics.

Recently, some manufacturers of cosmetic raw materials have proposed polyglycen (PGEs), such as polyglycerol esters of fatty acids, as alternatives to PEGs and ethoxylated emulsifiers. PGEs are biodegradable ingredients of plant origin, but as they can only be used in a narrow pH range (pH 4-8), they are not very useful in the field of hair colouring preparations. The main hair-dyeing methods are the semi-permanent system and the permanent oxidative system. The first involves the use of direct dyes which are deposited on the hair surface. Said compositions have a pH<5, and generally pH 3-4. With this system, the colour gradually fades every time the hair is shampooed, and eventually disappears within 10 washes.

The oxidative system is based on the reaction of "primary intermediates" with couplers; both of which are practically colourless. In the presence of air or oxidising agents such as hydrogen peroxide, primary dyes, which are typically primary aromatic amines with an additional hydroxyl or amino group, substituted or not substituted, in the para or ortho position, react with couplers (secondary dyes) such as resorcinol, m-aminophenol, m-phenylenediamine and 1-naphthol.

As the dye molecules thus formed in the cuticle are larger than the starting primary intermediates and the highly diffusible couplers, they remain trapped inside the hair, and there is therefore no significant fading due to successive washes or the action of external agents.

In this case the compositions have a pH>9, and the stability of the dye to washing ranges from four to eight weeks.

Hair colouring preparations in gel or emulsion-gel form are suitable to be formulated without ethoxylated ingredients because they do not contain emulsifiers, or contain low percentages thereof which can easily be replaced with natural alternatives without excessively increasing the formula costs.

However, hair colouring preparations in gel form require suitable viscosity-controlling agents that give the product suitable rheology and maintain it over time. They must also contain ingredients that give the product adherence, so that it does not drip from the head during application.

Suspending agents/solubilisers for dyes and fragrances must also be present.

U.S. Pat. No. 9,901,529 discloses an oxidative dye in gel form which requires not only the presence of a cellulose derivative, in particular hydroxyethylcellulose (ethoxylated ingredientj, but also at least one acrylate/methacrylamide copolymer and at least one crosslinked acrylic ormethacrylic; acid polymer.Said patent demonstrates the difficulty of creating gel formulations for oxidative dyes which offer high performance and stability despite using ethoxylated ingredients.

There is therefore a need to develop cosmetic compositions, particularly for hair colouring, characterised by the absence, or at least a low content, of ethoxylated products or ethylene oxide derivatives. The problem is not easy to solve in that ethoxylated ingredients, as well as being cheap, are very high performance and highly versatile; they enable formulators to modulate the viscosity and textures of cosmetic products easily in a wide pH range without any problems of stability over time.

U.S. Pat. No. 10,398,634 discloses hair-colouring process involving the use of 3 compositions to be mixed together: a colouring composition dye with pH 8-11, an oxidising composition with pH 1.5-5, and a composition with an acid pH containing a specific combination of organic acids. This latter composition contains a thickening polymer selected from hydroxypropyl xanthan gum, dehydroxanthan gum, xanthan gum, and polymeric anionic thickening agents. Hydroxypropyl xanthan gum, which is known to perform better as it is derivatised, is always used in the examples. However, the patent does not exclude ethoxylated ingredients, which are expressly listed among both thickening agents and surfactants.

DESCRIPTION OF THE INVENTION

It has now been found that a combination of xanthan gum and glyceryl glucoside allows the formulation of a hair colouring preparation in gel form, free of ethoxylated ingredients and PEGs, which, as well as possessing excellent rheological behaviour, stability over time and suitable adherence, also protects the hair against pollution.

The natural gum is preferably dehydrated xanthan gum.

Said composition does not contain ethanolamine (MEA) or ethoxylated alkalising agents.

Natural polysaccharides, including xanthan gum, are known to be biocompatible, non-toxic and biodegradable. However, virgin xanthan gum is known to have significant limitations on use because of its rheological behaviour and the instability of the viscosity over time, which means that it needs to be chemically modified in order to improve its performance (RCS Adv, 2020, 10, 27103).

Dehydrated xanthan gum is a natural polymer which, in water, generates a gelatinous gel with low adherence, and is therefore unsuitable for formulating hair colouring preparations.

Surprisingly, by combining dehydrated xanthan gum, in the amount of 0.5 to 2 weight percent of the weight of the composition, with glyceryl glucoside in the amount of 0.1 to 5 weight percent of the weight of the composition, a more fluid texture is obtained, with excellent adherence and suitable stability of the viscosity over time.

Glyceryl glucoside (marketed under the name of Hydagen® aquaporin or Glycoin® natural) is a wetting agent of natural origin used in skin care, but is not known to give formulations rheological properties or adherence, and is not used in hair colouring preparations.

In the context of the invention, "alkalising agent" or "alkaliser" means an ingredient or combination of ingredients able to adjust the pH of the cosmetic composition to a value above 7, generally between 9 and 11. For example, the alkaliser may be ammonia, arginine, lysine, monoisopropanolamine (MIPA), aminopropanol (2AP), dimethylglucamine (DMG), aminomethyl propanol (AMP), sodium hydroxide or potassium hydroxide. The alkaliser is not ethanolamine (MEA).

"Ethoxylated ingredients" means surfactants, viscosity-controlling agents, emulsifiers, solvents, conditioning and film-forming/fixative agents obtained by ethoxylation of alcohols, acids or triglycerides with ethylene oxide.

The alkaliser can be present in percentages ranging between 0.05 and 10%.

"Activator" means an agent able to promote the oxidation and coupling reaction between primary dyes and couplers. "Activator" means, for example, hydrogen peroxide, carbamide peroxide, perborates and persulphates or peracids, preferably hydrogen peroxide.

The activator can be mixed with the dye, generally at the ratio of 1:1 to 1:2, depending on the desired result. A smaller amount of activator promotes the concentration of the dyes, and is useful when the required performance is concealing grey hair; conversely, a larger amount of activator is useful for tonalising or providing fashionable highlights.

The mixture of dye and activator is left to act on the hair for 2 to 60 minutes at room temperature, and then rinsed off.

The composition according to the invention can be applied directly to the hair, in which case the activator is the oxygen present in the air, and the dye is called a "progressive" dye. In that case, the composition is left to act for 2 to 45 minutes, and optionally rinsed off.

The composition according to the invention can also contain direct dyes only, in which case it is applied to the hair without being mixed with an activator and left to act for 2 to 45 minutes.

The compositions according to the invention have a pH ranging from 3 to 11, depending on type (oxidative, direct or progressive).

The oxidative dye is preferably selected from 1-Acetoxy-2-Methylnaphthalene, 5-Amino-4-Chloro-o-Cresol, 4-Amino-m-Cresol, 3-Amino-2,4-Dichlorophenol, 3-Amino-2,4-Dichlorophenol, 2-Amino-5-Ethylphenol, 2-Amino-4-Hydroxyethylaminoanisole, 2-Amino-4-Hydroxyethylaminoanisole, 2-Amino-3-Hydroxypyridine, 4-Amino-2-Hydroxytoluene, m-Aminophenol, p-Aminophenol, 1,3 -Bis-(2,4-Diaminophenoxy)propane, 2,6-Bis(2-Hydroxyethoxy)-3,5-Pyridinediamine, N,N-Bis(2-Hydroxyethyl)-p-Phenylenediamine, 4-Chlororesorcinol, 2,4-Diamino-phenoxyethanol, 2,6-Diaminopyridine, 2,6-Dihydroxy-3,4-Dimethylpyridine, 2,6-Dihydroxyethylaminotoluene, Dihydroxyindole, 5,6-Dihydroxyindoline, 2,6-Dimethoxy-3,5-Pyridinediamine, 1-Hexyl 4,5-Diamino Pyrazole Sulphate, Hydroxyethyl-3, 4-Methylenedioxyaniline, Hydroxyethyl-p- Phenylenediamine, 6-Hydroxyindole, 6-Methoxy-2-methylamino-3-aminopyridine, 2-Methoxymethyl-p-Aminophenol, 2-Methoxymethyl-p-Phenylenediamine, 2-Methoxy-p-Phenylenediamine, p-Methylaminophenol, 2-Methyl-S-Hydroxyethylaminophenol, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, Phenyl Methyl Pyrazolone, resorcinol, tetraaminopyrimidine, toluene-2,5-diamine, p-phenylenediamine or salts thereof.

Examples of direct dyes include Acid green 25, Acid red 92, Acid red 95, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 99, Basic Blue 124, Basic Brown 4, Basic Brown 16, Basic Brown 17, Basic Orange 31, Basic Red 1, Basic Red 51, Basic Red 76, Basic Red 118, Basic Violet 2, Basic Violet 14, Basic Violet 16, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Disperse Blue 377, Disperse Violet 1, HC Blue No. 2, HC Blue No. 10, HC Blue No. 11, HC Blue No. 12, HC Blue No. 13, HC Blue No. 14, HC Blue No. 15, HC Blue No.16, HC Blue No. 17, HC Blue No. 18, HC Orange No. 1, HC Orange No. 2, HC Red No. 3, HC Red No. 10, HC Red No. 11, HC Red No. 13, HC Violet No. 1, HC Violet No.2, HC Yellow No. 2, HC Yellow No. 4, HC Yellow No. 11, HC Yellow No.13, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

The direct dye is preferably selected from Acid orange 7, Acid red 52, Acid red 33, Acid violet 43, Acid yellow 1, Acid yellow 23, Acid red 92 and Acid black 1.

The compositions according to the invention may also contain one or more natural or synthetic additives commonly used in the cosmetic industry, such as solvents, surfactants, viscosity-controlling agents, rheological agents and conditioning agents.

Examples of solvents include water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular those having 2 to 6 carbon atoms, such as 1,3-propanediol, 1,4-butanediol, 1,5-pentanediol, 1,6-hexanediol, 1,2,6-hexanetriol, glycerin, butylene glycol, dimethyl-isosorbide and propylene carbonate.

Examples of emulsifiers include cetearyl olivate, sorbitan olivate or a mixture thereof (Olivem 1000® from Hallstar); polyglyceryl-2 stearate, polyglyceryl-2-oleate, glyceryl stearate or mixtures thereof (Polyaquol 2W® and Polyaquol OS2®), oleic acid, stearic acid and polyglyceryl-6 distearate.

Examples of non-ionic/amphoteric and anionic surfactants are glycolipids, alkylbenzene sulphonates, olefin sulphonates, cocamidopropyl betaine, coco glucoside, decyl glucoside, lauryl glucoside, capryloyl/caproyl methyl glucamide, lauroyl/myristoyl methyl glucamide, cocoyl methyl glucamide, sodium methyl cocoyl taurate, sodium lauroyl methyl isethionate, sodium cocoyl glutamate, sodium lauroyl glutamate, sodium lauroyl sarcosinate and sodium stearoyl lactylate.

Examples of cationic surfactants include quaternary ammonium compounds, ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other useful cationic surfactants are quaternised protein hydrolysates and stearamidopropyl dimethylamine.

Examples of conditioning agents/humectants comprise quaternium 80, quaternium 87, polyquaternium-39, polyglyceryl-3 betainate acetate, isoamyl laurate panthenol, vitamins and pro-vitamins, plant extracts and sugars.

The composition can advantageously contain film-forming/fixative agents such as vinylpyrrolidone/vinyl acetate copolymer (VP/VA copolymer) and sodium polyitaconate.

The composition can advantageously contain viscosity-controlling agents/rheological additives such as carbomer, sodium polyacrylate, rice starch, tara gum, gellan gum and C12-C15 alkyl lactate.

Finally, auxiliary agents such as electrolytes, antioxidants, sequestering agents and preservatives may be present.

The invention will be described in detail in the following examples, wherein the ingredients reported are named with the INCI nomenclature (European Community Decision 2006/257/EC as amended—International Nomenclature of Cosmetic Ingredients).

Table 1 shows formulas F1 to F7 according to the invention.

The amounts of the ingredients are expressed as weight percent compared with the weight of the composition.

TABLE 1

Permanent hair colouring gel preparations, shade 6, according to the invention

| ingredients | F1 % | F2 % | F3 % | F4 % | F5 % | F6 % | F7 % |
| --- | --- | --- | --- | --- | --- | --- | --- |
| AQUA (WATER) | q.s. to 100 | q.s. to 100 | q.s. to 100 | q.s. to 100 | q.s. to 100 | q.s. to 100 | q.s. to 100 |
| PROPANEDIOL | 7 | 7 | 7 | 7 | 7 | 7 | 7 |
| SODIUM HYDROXIDE | 1 | 1 | 1 | — | — | — | — |
| POTASSIUM HYDROXIDE | — | — | — | 1.4 | — | — | — |
| AMMONIA | 1.8 | 1.8 | 1.8 | 1.8 | 1.8 | 1.8 | — |
| DIMETHYL GLUCAMINE | — | — | — | — | 7.4 | — | — |
| L-ARGININE | — | — | — | — | — | 4 | 6 |
| DEHYDROXANTHAN GUM | 1.5 | 1 | 1 | 1 | 1 | 1 | 1 |
| GLYCERYL GLUCOSIDE | 1 | 1 | 1 | 1 | 1 | 1 | 1 |
| CARBOMER | — | — | 0.3 | — | — | — | — |
| VP/VA COPOLYMER | — | 0.5 | — | — | — | — | — |
| GLYCOLIPIDS | 0.8 | 0.8 | 0.8 | 0.8 | 0.8 | 0.8 | 0.8 |
| PARFUM (FRAGRANCE) | 0.8 | 0.8 | 0.8 | 0.8 | 0.8 | 0.8 | 0.8 |
| SODIUM SULPHITE | 0.4 | 0.4 | 0.4 | 0.4 | 0.4 | 0.4 | 0.4 |
| ISOASCORBIC ACID | 0.4 | 0.4 | 0.4 | 0.4 | 0.4 | 0.4 | 0.4 |
| TETRASODIUM EDTA | 0.26 | 0.26 | 0.26 | 0.26 | 0.26 | 0.26 | 0.26 |
| TOLUENE-2,5-DIAMINE SULPHATE | 0.615 | 0.615 | 0.615 | 0.615 | 0.615 | 0.615 | 0.615 |
| RESORCINOL | 0.6 | 0.6 | 0.6 | 0.6 | 0.6 | 0.6 | 0.6 |
| m-AMINO PHENOL | 0.142 | 0.142 | 0.142 | 0.142 | 0.142 | 0.142 | 0.142 |
| 2,4-DIAMINOPHENOXYETHANOL HCl | 0.12 | 0.12 | 0.12 | 0.12 | 0.12 | 0.12 | 0.12 |

Table 2 shows Formula C1 made according to U.S. Pat. No. 9,901,529 used as comparative formula.

TABLE 2

Permanent hair colouring gel preparation, shade 6 (comparative formula)

| ingredients | C1 % |
| --- | --- |
| AQUA (WATER) | q.s. to 100 |
| PROPYLENE GLYCOL | 7 |
| HYDROXYETHYL CELLULOSE | 2.4 |
| AMMONIA | 1.8 |
| ETHANOLAMINE | 1 |
| CARBOMER | 0.5 |
| ACRYLATES/METHACRYLAMIDE COPOLYMER | 0.1 |
| PEG-40 HYDROGENATED CASTOR OIL | 0.5 |
| PARFUM (FRAGRANCE) | 0.8 |
| SODIUM SULPHITE | 0.4 |
| ISOASCORBIC ACID | 0.3 |
| EDTA | 0.14 |
| TOLUENE-2,5-DIAMINE SULPHATE | 0.615 |
| RESORCINOL | 0.6 |
| m-AMINO PHENOL | 0.142 |
| 2,4-DIAMINOPHENOXYETHANOL HCl | 0.12 |

Table 3 shows an example of a permanent dye in the form of an emulsion gel according to the invention.

TABLE 3

Oxidative dye shade 6, in emulsion-gel form

| ingredients | F8 % |
|---|---|
| AQUA (WATER) | q.s. to 100 |
| PROPANEDIOL | 7 |
| CETEARYL ALCOHOL | 7.5 |
| GLYCERYL STEARATE | 1.5 |
| SODIUM HYDROXIDE | 1 |
| AMMONIA | 1.8 |
| DEHYDROXANTHAN GUM | 1 |
| GLYCERYL GLUCOSIDE | 1 |
| GLYCOLIPIDS | 0.8 |
| PARFUM (FRAGRANCE) | 0.8 |
| SODIUM SULPHITE | 0.4 |
| ISOASCORBIC ACID | 0.4 |
| TETRASODIUM EDTA | 0.26 |
| TOLUENE-2,5-DIAMINE SULPHATE | 0.615 |
| RESORCINOL | 0.6 |
| m-AMINO PHENOL | 0.142 |
| 2,4-DIAMINOPHENOXYETHANOL HCl | 0.12 |

Table 4 shows an example of a direct dye according to the invention.

TABLE 4

Formula F9, example of a formula with direct dyes according to the invention.

| ingredients | % |
|---|---|
| AQUA (WATER) | q.s. to 100 |
| ACID ORANGE 7 | 0.5 |
| ACID BLACK 1 | 0.5 |
| ACID RED 33 | 0.05 |
| DENAT. ALCOHOL | 5 |
| PROPYLENE CARBONATE | 20 |
| DEHYDROXANTHAN GUM | 1 |
| LACTIC ACID | 4.5 |
| GLYCERYL GLUCOSIDE | 0.5 |
| GLYCERIN | 0.5 |
| SODIUM HYDROXIDE | 0.17 |
| SODIUM BENZOATE | 0.1 |

Table 5 shows an example of a progressive dye according to the invention.

TABLE 5

Formula F10, example of a progressive hair colouring preparation according to the invention

| Ingredient | % |
|---|---|
| AQUA (WATER) | to 100 |
| 5,6-DIHYDROXYINDOLINE HBR | 0.5 |
| TRISODIUM ETHYLENEDIAMINE DISUCCINATE | 0.25 |
| L-ARGININE | 0.9 |
| ISOASCORBIC ACID | 0.5 |
| SODIUM SULPHITE | 0.8 |
| DEHYDROXANTHAN GUM | 1.2 |
| GLYCERYL GLUCOSIDE | 0.5 |
| DIMETHYL GLUCAMINE | 5 |
| PROPANEDIOL | 5 |

EXAMPLE 1: ADHERENCE

Adherence is an important parameter for hair colouring preparations, which must adhere well to the hair and not drip during the colour development time, which ranges from 5 to 60 minutes.

The test is conducted with a DIAS-TRON MTT175-Miniature Tensile Tester-tack/adhesion accessory.

The adherence test is conducted by measuring the adherence between two circular plates repeatedly pressed together and separated.

The parameters set are:
1) The separation distance between the plates during each cycle (mm): setting a low value accelerates the cycle times.
2) The contact force (g) determines the force with which the plates are pressed together at the start of each cycle. It should be set on the basis of the viscosity of the sample. A value ranging from 20 to 50 g is typical for the majority of liquids and creams.
3) The speed (mm/min) determines the rate at which the plates are separated, typically 200 to 2000 mm/min.
4) The contact time (s) is the time for which the plates must be held together before being separated.
5) The lag time (s) sets the delay between one cycle and the next.
6) The number of cycles sets the number of repetitions.

The contact force between the plates is shown in the bottom left-hand corner of the chart in FIG. 1.

In each cycle, when the plates are separated, the instrument measures a force that gradually approaches zero, as the spring in the bottom plate relaxes. The turning peak then appears while the plates are separated.

The adherence of the sample is equal to the area under the peak curve (indicated by an arrow), and represents the work performed to separate the 2 plates. The greater the work, the greater the adherence of the product. The test was conducted by setting the following parameters:
1) separation distance of plates during each cycle: 30 mm
2) contact force: 50 g.
3) speed: 200 mm/min.
4) contact time: 3 s.
5) lag time: 1 s.
6) number of cycles: 2.

Formulas F1, F2, F3 and C1 were placed on the plate, each mixed with the activator Alfaparf Oxid'o 40 vol, at the ratio of 1: 1.5. Table 6 shows the results obtained.

TABLE 6

Total average work

| Treatment | Total average work (joules) |
|---|---|
| Formula F1 | 0.00139 |
| Formula C1 | 0.00140 |
| Formula F3 | 0.00140 |
| Formula F2 | 0.00153 |

As shown in the table, the adherence of Formulas F1 and F3 (without ethoxylates) is comparable to that of Formula C1 (with ethoxylates). Formula F3 is actually slightly better.

EXAMPLE 2: ANTI-POLLUTION TESTS

The impact of environmental pollutants on the hair is well known, and it has become increasingly important to market products that protect the hair.

Treated hair, especially hair coloured with oxidative dyes, is far more sensitive to pollution than natural hair.

Cigarette smoke can be used to simulate indoor and outdoor environmental pollutants. Exposure to cigarette smoke is known to make the hair less manageable and more difficult to comb.

Formulas C1, F2 and F3 are each mixed with the activator Alfaparf Oxid'o 20 vol at the ratio of 1:1.5, and each one is applied to 3 locks of IHIP level 10 hair (very light blonde). After 35 minutes at 30° C. the locks are rinsed with water and dried for 30 minutes in a dryer.

The combability of the 9 locks, and of 3 untreated (undyed) IHIP level 10 locks, is measured with a DIASTRON MTT175- Miniature Tensile Tester-tack/combing accessory.

The locks are fixed to the top of the instrument, combed from top to bottom 10 times, and the average work performed by the comb is recorded. The greater the work, the lower the combability.

The 12 locks are then placed in a closed box and subjected to the smoke of 8 cigarettes.

The combability measurement is then repeated. The locks are then washed with a shampoo base containing 9% sodium laureth sulphate, dried in the dryer, and the combability measurement repeated again.

The resulting data, expressed as greater or lesser % work required to comb the locks, compared with the work performed before exposure to cigarette smoke, are set out below:

TABLE 7

% variation in total work.

|  | % total work |
|---|---|
| Formula C1 | |
| AFTER 8 CIGARETTES | +157% |
| AFTER WASHING | +36% |
| Formula F2 | |
| AFTER 8 CIGARETTES | +1% |
| AFTER WASHING | −30% |
| Formula F3 | |
| AFTER 8 CIGARETTES | +18% |
| AFTER WASHING | −42% |
| Untreated hair | |
| AFTER 8 CIGARETTES | +48% |
| AFTER WASHING | +39% |

The results demonstrate that the untreated locks become about 50% less combable due to exposure to cigarette smoke, and only partly recover their original combability after washing.

The locks prepared with formula C1 (gel with ethoxylates) exhibit about 150% worse combability, demonstrating that treated hair is more sensitive to pollution than normal hair. After washing, the hair regains much, but not all, of its combability.

The combability of the locks dyed with formulas F2 and F3 according to the invention is surprisingly very little worse after exposure to pollution, and even more surprisingly, their combability after washing is better than that of hair not yet exposed to pollution. The formulas according to the invention therefore exhibit not only a highly protective effect against pollutants, but also a purifying/conditioning effect.

As cigarette smoke is known to contain heavy metals, the purifying effect of the hair colouring preparations according to the invention is probably also a metal-detox effect.

Removing metal residues from hair is very important, especially in the field of oxidative dyeing, because metals can cause undesirable reactions that generate an unexpected colour, as well as damaging the hair.

The invention claimed is:

1. A hair colouring compositions in gel or emulsion-gel form comprising dehydroxanthan gum, glyceryl glucoside, at least one dye and additives, provided that the additives do not comprise ethoxylated ingredients, ethanolamine or polyethylene glycols.

2. The composition according to claim 1 wherein the additives are selected from solvents, surfactants, viscosity-controlling/rheological agents, conditioning agents and filming/fixative agents.

3. The composition according to claim 1 containing 0.5 to 2 wt % of dehydroxanthan gum and 0.1 to 5 wt % of glyceryl glucoside.

4. The composition according to claim 1 comprising one or more direct dyes.

5. The composition according to claim 1 comprising one or more oxidative dyes.

6. The composition according to claim 1 comprising vinyl pyrrolidone/vinyl acetate (VP/VA copolymer) and/or sodium polyitaconate.

7. The composition according to claim 1 comprising viscosity-controlling/rheological agents selected from carbomer, sodium polyacrylate, rice starch and C12-C15 alkyl lactate.

* * * * *